United States Patent [19]

Lieb et al.

[11] E Re. 29,817

[45] Reissued Oct. 31, 1978

[54] DENTAL PIN

[75] Inventors: Nathaniel H. Lieb, Narberth; Richard A. Wallace, Audubon, both of Pa.

[73] Assignee: Star Dental Manufacturing Co. Inc., Conshohocken, Pa.

[21] Appl. No.: 758,873

[22] Filed: Jan. 12, 1977

Related U.S. Patent Documents

Reissue of:

[64] Patent No.: 3,861,043
Issued: Jan. 21, 1975
Appl. No.: 350,235
Filed: Apr. 11, 1973

[51] Int. Cl.[2] ..... A61K 5/02
[52] U.S. Cl. ..... 32/15
[58] Field of Search ..... 32/5, 13, 15, 7, 6

[56] References Cited

U.S. PATENT DOCUMENTS

| | | | |
|---|---|---|---|
| 114,454 | 5/1871 | Mack | 32/15 |
| 143,418 | 9/1873 | Osmond | 31/15 |
| 2,472,103 | 6/1949 | Giesen | 32/15 |
| 3,590,485 | 7/1971 | Chercheve | 32/10 A |
| 3,675,328 | 7/1972 | Weissman | 32/15 |
| 3,675,329 | 7/1972 | Weissman | 32/15 |

FOREIGN PATENT DOCUMENTS

| | | | |
|---|---|---|---|
| 13,918 of | 1895 | United Kingdom | 32/13 |

*Primary Examiner*—Robert Peshock
*Attorney, Agent, or Firm*—Joseph I. Hirsch; William B. Walker

[57] ABSTRACT

A dental pin used in building a superstructure on a tooth having a substantial portion thereof that has been removed. The pin comprises a shaft having a flute at the lower end thereof. The remainder of the shaft is threaded. The flute taps a hole that has previously been drilled in the tooth, and the threads on the shaft are retained in the tapped hole. Thus, the shaft is self-tapping. The shaft also includes an integral handle which permits the rotating of the pin into the tooth. A plurality of the pins are inserted in the tooth in a non-parallel relationship, and a superstructure is built on exposed portions of the pins. A fracture point is formed on each pin in order to break the head off after the pin has been inserted.

11 Claims, 5 Drawing Figures

FIG. 1
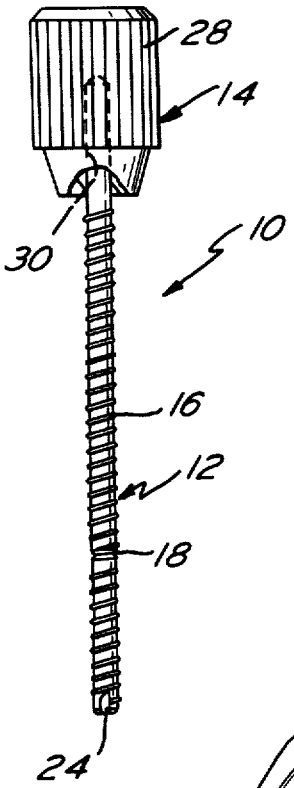
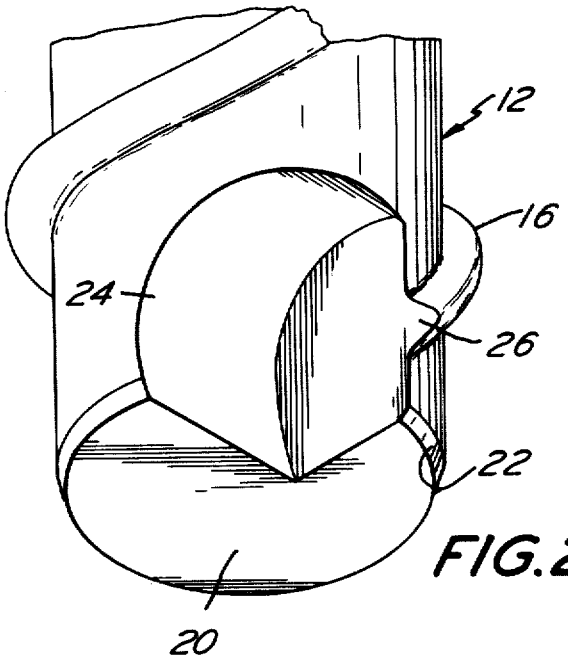
FIG. 2
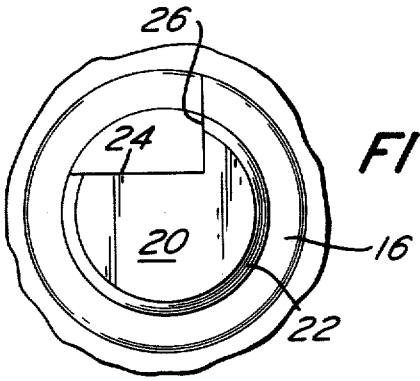
FIG. 3
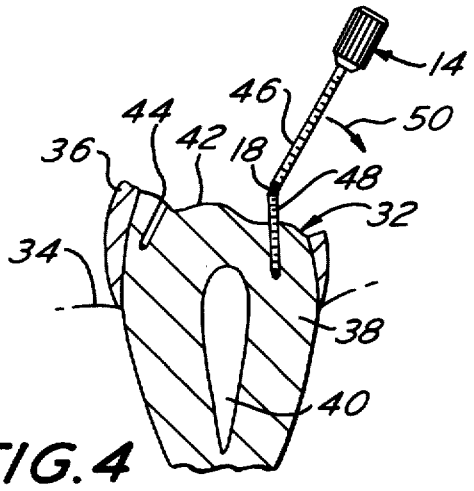
FIG. 4
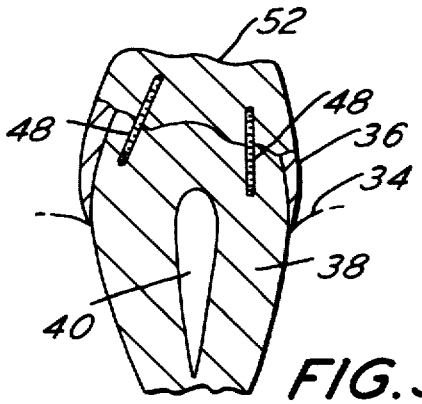
FIG. 5

DENTAL PIN

Matter enclosed in heavy brackets [ ] appears in the original patent but forms no part of this reissue specification; matter printed in italics indicates the additions made by reissue.

This invention relates to a dental pin used in reconstructing a tooth, and more particularly, to a dental pin that is used in providing an anchor for a superstructure built on a severely excavated tooth.

It is now a common practice in restorative dentistry to build a superstructure on a tooth that has been badly damaged, as by decay or by breaking. These superstructures are held in place on the tooth by pins that are first secured in the tooth in a non-parallel relationship. The pins are held in place either by a pressure fit, by cement or by a self-threading action.

The self-threading pin is disclosed in U.S. Pat. No. 3,675,328. As disclosed in that patent, the pin is used by first drilling a plurality of holes in a broken or excavated tooth and then threading a plurality of anchors into the holes. Each of the anchors or pins is self-threading. Although not disclosed in the patent, the self-threading action of the pin is accomplished by using a sharp edged thread on the pin which forces the dentin out of the way as the pin is threadedly advanced therein.

It should be noted that each tooth comprises an outer shell of enamel, an inner dentin portion and a pulp channel which is surrounded by the dentin. The dental pins of the prior art and of this invention are all retained in the dentin. The properties of dentin have not been precisely determined, but it is a brittle material having a compressive strength in the range of 36,000 to 40,000 psi, and a tensile strength between 3,100 and 7,300 psi. Its modulus of elasticity has been reported between 550,000 and 3,150,000 psi.

Self-threading pins work reasonably well in ductile, elastic materials, but in brittle, rigid materials stress concentrations and ring tensions around the hole in which they are being threaded often cause the material to crack. Even when cracking does not occur, deleterious stresses are induced in brittle base materials. Therefore, the use of the self-threading pins creates a constant stress in a tooth in which they are used.

On the other hand, if a brittle material is tapped, the tapping action takes a certain portion of the material away by the removal of a chip, and the resulting structure is left with no residual internal stresses of any consequence. It is based on this realization that the instant invention was developed. Thus, the dental pins of this invention, rather than being self-threading, are self-tapping. A flute is placed in the bottom of the dental pin leaving a sharp cutting edge which actually cuts a helical path through the tooth, and removes a portion of the tooth as the path is cut. The self-tapping is done by the starting thread only, leaving the rest of the threads intact, for maximum holding ability to the dentin.

Since the threads themselves need do no threading in the instant invention, they are arcuate in shape, and provide no stresses on the cut thread.

Additionally, since all stress is eliminated by tapping the thread, there can be greater depth of penetration of the thread into the dentin. Thus, where using the self-threading pins, only a very shallow penetration into the dentin by the threads can be obtained, or else the stresses would be so great that the tooth would crack or rupture. Contrasted with this, once the tapping flute has removed a portion of the dentin, there can be greater depth of penetration of the thread into the tooth, thereby giving a more secure anchor.

Another feature of the dental pin of this invention is the provision of an integral handle on the pin. This handle has a diameter which is substantially greater than the diameter of the shaft of the pin, and accordingly facilitates the picking up of the pin for use. After a hole has been drilled in the tooth, the pin is picked up by the handle and rotated into place. A fracture point is provided for each pin, and after the pin has been inserted, the handle and the upper portion of the pin are removed by bending the pin at the fracture point.

In all of the pins of the prior art, the handle was separate from the pin, and the pin was provided with a flattened blade portion which is adapted to receive the handle. See, for instance, aformentioned U.S. Pat. No. 3,434,209 and U.S. Pat. Nos. 3,675,328 and 3,675,329. In all of these prior patents, the blade portion was of substantially the same width as the remainder of the pin, and accordingly did not faciliate the picking up of the pin. Additionally, since the blade portion was flat on two sides, it could not be rotated to insert the pin, but instead a separate wrench was necessary.

It is accordingly an object of this invention to provide a novel dental pin.

It is another object of this invention to provide a dental pin having a self-tapping leading thread.

It is a further object of this invention to provide a dental pin having an integral handle.

It is yet a further object of this invention to provide a method of building a superstructure on a tooth utilizing the novel pin of this invention.

These and other objects of this invention are accomplished by providing a dental pin comprising a shaft, a thread formed on said shaft, and means for tapping a thread in a tooth on said shaft, said tapping means comprising a cutting edge on the leading edge of the thread.

Other objects and many of the attendant advantages of this invention will be readily appreciated as the same becomes better understood by reference to the following detailed description when considered in connection with the accompanying drawings wherein:

FIG. 1 is a front elevational view, partly broken away, showing the dental pin of this invention;

FIG. 2 is an enlarged perspective view of the leading edge of the dental pin of this invention;

FIG. 3 is a bottom plan view of the dental pin of this invention;

FIG. 4 is a sectional view of a tooth showing the method of using a dental pin of this invention; and FIG. 5 is a sectional view of a tooth that has been reconstructed using a plurality of dental pins of this invention.

Referring now in greater detail to the various figures of the drawings wherein like reference characters refer to like parts, a dental pin embodying the present invention is generally shown at 10 in FIG. 1. Device 10 basically comprises a shaft 12 and a handle 14 which is integral with the shaft.

As seen in FIG. 1, shaft 12 has a thread 16 which extends along the entire length of the shaft, and terminates just short of the handle 14. As seen in FIG. 2, the thread 16 has a rounded or arcuate outer edge. Shaft 12 includes an intermediate annular fracture groove 18.

The bottom 20 of the shaft 16 is flat, and includes a small bevelled edge 22.

A cut is made in the bottom face of shaft 12, leaving a slot 24. The slot 24 can be formed by any means known to the art, such as an end mill or a file. When the slot 24 is cut, it leaves a sharp leading edge 26 on the thread 16 (FIG. 2).

Referring to FIG. 1, it is seen that the handle 14 has a diameter that is substantially larger than that of the shaft 12. The handle 14 is circular in cross section, and has an outer roughened surface which can be formed by grooves 28 or by knurling. The handle has an internal bore 30, and is secured on shaft 12 by a pressed fit. If desired, the handle can additionally be secured in place by a pin passing through the handle and the shaft 12.

In the embodiment shown, the shaft 12 is threaded only up to the handle 14, and is smooth on its outer surface from that point on. If desired, the shaft 12 can be formed from threaded stock, and the threaded portion will project into the handle. The dental pin 10 will carry out its intended function, regardless of whether the threads 16 pass into the handle.

The dental pin of this invention is used in the same manner as the dental pin of the prior art referred to above. Thus, the pin is used in the reconstruction of a severely decayed or damaged tooth, which is generally shown at 32 in FIG. 4. The tooth is in the soft tissue or gingiva 34 of the human gum. The tooth includes the enamel 36 which covers the dentin 38. The dentin in turn encloses a pulp channel 40. Prior to reconstructing the tooth, a portion of the enamel and a portion of the dentin are excavated in order to remove decayed and undermined understructure, thereby forming the excavated surface 42, which is free of decay.

In order to build a superstructure on the remaining portion of the tooth 32, the first step in using the dental pins of this invention is to drill a plurality of holes 44 into the dentin. These holes have a diameter which is slightly smaller than the outer diameter of the threads 16 of the pin 10. The difference in diameter is in the order of 0.002 to 0.003 inch. Thereafter, a dental pin 10 is threaded into each of the holes 44. This is accomplished by placing the bottom of the pin adjacent the entrance to a hole 44 and rotating the handle 14 between the thumb and forefinger. When this is done, the leading edge 26 actually cuts a helical path through the dentin, and the remainder of the pin is threaded along this path by applying a rotational force on the handle and a slight downward pressure against the tooth.

After the pin has reached its desired depth, which is determined by the depth of the pre-drilled hole, the handle 14 and the upper portion 46 of the shaft are removed. This is accomplished by bending the shaft 12 at the fracture groove 18, which is easily accomplished once the lower portion 48 of the shaft is inserted in its hole. Thus, the fracture groove is sufficiently strong to take the torque or twisting motion of inserting the shaft, but is sufficiently weak to break when a bending force is applied to the fracture groove, as shown by the arrow 50 in FIG. 4.

The lower portions 48 of the shafts serve as anchors for building the superstructure on the excavated tooth. As seen in FIG. 5, the anchors 48 are all in a non-parallel relationship to each other the number of anchors used can vary, depending on the size of the tooth and the amount of the superstructure that is to be built thereon. Once the anchors 48 are in place, the superstructure 52 is built on the exposed excavated surface 42. Any material known to the art can be used for the superstructure. By way of example, the superstructure can be gold foil, silver restoration material or a self-curing resin.

The superstructure 52 is retained on the exposed portions of the anchors 48. The threads 16 aid in the retention of the superstructure, as does the angular relationship between the anchors 48. Thus, the firmly threaded anchors 48 serve to anchor the superstructure in position and reinforce its securement to surface 42.

It is thus seen that the dental pins of this invention are used in the same manner as the dental pins in the prior art, as exemplified by the patents cited above. The pins are used in a non-parallel relationship to each other on the tooth in order to insure better anchoring of the superstructure which is built on the tooth. The provision of the integral handle or head [22] *14* greatly facilitates the use of the pin of this invention over the use of the pins of the prior art. Thus, there is no problem of releasably securing a wrench to the small pins whenever it is desired to use the pins. Instead, the handle 28 is used for inserting the pins in place.

Another advantage of the handle is that it facilitates the picking up of a pin for use. The pins are extremely small in diameter, with the diameter being on the order 0.028 inch, and are accordingly most difficult to handle. However, by providing the integral handle which has a diameter of approximately five times the diameter of the pin, it is much easier to manipulate the pins and pick them up for use.

Another advantage of the pins of this invention is the provision of the self-tapping cutting edge at the leading edge of the thread. This shears the dentin when the pin is inserted, and taps a threaded hole for the pin. Contrasted with this, the self-threading pins act by crushing the dentin when the pin is inserted. This results inaa constant force on the tooth, and has a tendency to burst the tooth. Utilizing the self-tapping pins of this invention, the danger of cracking the tooth at the time of insertion and the subsequent rupture of the tooth as the stressed are maintained is eliminated.

The pins of this invention can be made in any sizes that are used for the prior art pins or in any sizes which are readily adaptable for use in a given tooth. By way of non-limiting example, the pins of this invention can have an overall length of 0.689 inch. The outer diameter of the pins at the threads is 0.028 inch and the threads have a height of 0.0035 inch. The fracture groove is approximately 0.05 inch from the lower tip of the pin, and has a diameter of 0.0175 inch the handle or head 28 has an outer diameter of 0.137 inch. Of course, it is to be understood, that the foregoing dimensions are solely by way of example, and obviously can be varied to suit the needs for any give tooth or operative procedure.

The pins can be made from any material known to the art. By way of example, stainless steel is a preferred material. If desired, the pins can also be given a gold-plated surface.

Although the invention has been described with respect to the use of a plurality of pins, it should be understood that the invention can be carried out with as little as one pin. However, when at least two pins are used in a non-parallel relationship, retention of the superstructure is improved.

Without further elaboration, the foregoing will so fully illustrate my invention, that others may, by applying current or future knowledge, readily adapt the same for use under various conditions of service.

What is claimed as the invention is:

1. A dental pin comprising a shaft, a thread formed of said shaft, said thread having an arcuate outer edge, said shaft having a lower end, and means for tapping a thread in a tooth on said shaft, said tapping means comprising a cutting face on said thread, said cutting face being formed as the leading edge of said thread, said cutting face being formed at the lower end of said shaft, said shaft having a flute formed on the bottom thereof, said thread terminating at said flute, and said cutting face comprising the leading edge of said thread adjacent said flute.

2. A dental pin comprising a shaft *having a flute formed at the lower end thereof* a thread formed on said shaft, *said thread terminating at said flute,* said thread having an accuate outer edge, means *on said shaft* for tapping a thread in a tooth [on said shaft], said tapping means comprising a cutting face on said thread, said cutting face being formed as the leading edge of said thread *at the intersection of said flute with said thread,* [said cutting face being formed at the lower end of said shaft,] and a handle on said shaft, said handle being integral with said shaft and positioned at the end of said shaft opposite said cutting face, said handle being circular in cross-section and having a diameter which is substantially larger than the diameter of said shaft, *whereby said handle facilitates the manual rotation of said pin when being inserted into a hole drilled in the tooth.*

3. A dental pin comprising a shaft *having a flute formed at the lower end thereof,* a thread formed on said shaft, [said shaft having a lower end,] *said thread terminates at said flute,* means *on said shaft* for tapping a thread on a tooth [on said shaft], said tapping means comprising a cutting face on said thread, said cutting face being formed as the leading edge of said thread *at the intersection of said flute with said thread,* [said cutting face being formed at the lower end of said shaft,] and a handle on said shaft, said handle being integral with said shaft, and positioned on the end of said shaft opposite said cutting face, said handle being circular in cross-section and having a diameter which is at least five times the diameter of said shaft *whereby said handle facilitates the manual rotation of said pin when being inserted into a hole drilled in the tooth.*

4. The dental pin claim 3 wherein said handle is secured to said shaft by a pressed fit.

5. The dental pin of claim 3 wherein said handle has a roughened outer surface.

6. The dental pin of claim 5 wherein said roughened outer surface is provided by a plurality of grooves in said handle.

7. The dental pin of claim 3 and further including a fracture groove of reduced thickness formed on said shaft, said fracture groove being formed between said cutting face and said handle.

[8. A method of securing a dental pin of a specific diameter in a tooth comprising drilling at least one channel from a tooth surface into the tooth dentin, the diameter of said channel being smaller than the diameter of the dental pin, said dental pin being threaded, with the thread having an arcuate outer edge, and said dental pin having a self-tapping cutting face on the leading edge of said thread, and progressively introducing said dental pin into said channel by rotating the same so as to cut a helical thread on the interior wall of said channel by the self-tapping action of said dental pin, and whereby the arcuate thread fills said cut thread in order to obtain maximum holding force on the dental pin, while the same time residual stresses are minimized by the cut helical thread.]

[9. The method of claim 8 wherein a plurality of said channels are drilled in said tooth and one of said dental pins is inserted in each of said channels, and further including the step of building a superstructure on the tooth about portions of said dental pins which project above the tooth surface.]

[10. The method of claim 9 wherein said dental pins are inserted into said tooth in a non-parallel relationship.]

*11. A dental pin comprising a shaft having a flute formed at the lower end thereof, a thread formed on said shaft, said thread terminating at said flute, means on said shaft for tapping a thread in a tooth, said tapping means comprising a cutting face on said thread, said cutting face being formed as the leading edge of said thread at the intersection of said flute with said thread, and a handle on said shaft, said handle being integral with said shaft and positioned to the end of said shaft opposite said cutting face, said handle having a dimension transverse to the axis of said shaft which is substantially larger than the diameter of said shaft, whereby said handle facilitates the manual rotation of said pin when being inserted into a hole drilled in the tooth.*

*12. The dental pin of claim 11 wherein said shaft has a fracture groove of reduced thickness between said cutting face and said handle.*

*13. A dental pin comprising a shaft having a flute formed at the lower end thereof, a thread formed on said shaft, said thread terminating at said flute, means on said shaft for tapping a thread in a tooth, said tapping means comprising a cutting face on said thread, said cutting face beng formed as the leading edge of said thread at the intersection of said flute with said thread, and a handle on said shaft, said handle being integral with said shaft and positioned on the end of said shaft opposite said cutting face, said handle having a dimension transverse to the axis of said shaft which is at least five times the diameter of said shaft, whereby said handle facilitates the manual rotation of said pin when being inserted into a hole drilled in the tooth.*

*14. The dental pin of claim 13 wherein said shaft has a fracture groove of reduced thickness between said cutting face and said handle.*

* * * * *